| United States Patent [19] | [11] Patent Number: 4,564,013 |
| Lilenfeld et al. | [45] Date of Patent: Jan. 14, 1986 |

[54] SURGICAL FILAMENTS FROM VINYLIDENE FLUORIDE COPOLYMERS

[75] Inventors: Robert Lilenfeld, Flemington; Nicholas M. Popadiuk, Raritan; Peter Steinheuser, Manville; Edgar Menezes, Somerville, all of N.J.

[73] Assignee: Ethicon, Inc., Somerville, N.J.

[21] Appl. No.: 613,558

[22] Filed: May 24, 1984

[51] Int. Cl.$^4$ ............................................. C08F 14/22
[52] U.S. Cl. .................................. 128/335.5; D623/1
[58] Field of Search ........................... 128/335.5; 3/1.4

[56] References Cited

U.S. PATENT DOCUMENTS 4,052,550 10/1977 Chion et al. .................... 526/255
4,353,960 10/1982 Endo et al. ...................... 428/373

*Primary Examiner*—C. Fred Rosenbaum
*Assistant Examiner*—Sherri E. Vinyard
*Attorney, Agent, or Firm*—Charles J. Metz

[57] ABSTRACT

Surgical filaments are made from a copolymer of vinylidene fluoride and hexafluoropropylene.

9 Claims, No Drawings

SURGICAL FILAMENTS FROM VINYLIDENE FLUORIDE COPOLYMERS

The invention relates to surgical filaments such as sutures and ligatures made from vinylidene fluoride copolymers.

BACKGROUND OF THE INVENTION

Surgical filaments are made from a wide variety of materials in order to satisfy the full range of surgical and medical needs. Illustrative materials from which surgical filaments are made are surgical gut, silk, cotton, steel, nylon, polyester, polypropylene, lactide homopolymers and copolymers, polydioxanone, and others. Despite the many different materials from which surgical filaments are now made, there is a continuing search for new materials in the hope of improving deficiencies of the currently available materials, or in the hope of providing combinations of properties not presently obtainable.

It has recently been proposed to produce surgical sutures from polyvinylidene fluoride. It was observed, for instance, that such sutures have very high tensile and knot strength. The inventors herein have found, however, that the compliance (as is evidenced by the Young's modulus) of monofilaments made from polyvinylidene fluoride homopolymer is a little high, thereby limiting the utility of monofilament sutures made from such materials. The inventors herein have also found that if one subjects vinylidene fluoride homopolymer monofilament to an annealing with relaxation or shrinkage step so as to reduce the Young's modulus, and thereby increase the compliance, the elongation of such monofilaments is increased to the point where the monofilament is very "stretchy", and therefore its usefulness is reduced.

This invention is based upon the discovery that certain vinylidene fluoride copolymers can be fabricated into surgical filaments that have an excellent combination of properties, including acceptable tensile and knot strength as well as excellent compliance.

BRIEF SUMMARY OF THE INVENTION

The invention provides surgical filaments such as sutures and ligatures made from copolymers of vinylidene fluoride and hexafluoropropylene.

THE PRIOR ART

German Utility Model (Gebrauchsmuster) No. 82 21 647, to Dynamit Nobel AG, discloses surgical sutures made from "polyvinylidene fluoride." Only the homopolymer appears to be contemplated by the disclosure. An equivalent disclosure is found in published German patent application No. 32 28 428, published on Feb. 9, 1984.

Chion et al., in U.S. Pat. No. 4,052,550, disclose "poly(vinylidene fluoride)yarns and fibers." At Col. 1, lines 44-49, the patentees state that poly(vinylidene fluoride) is intended to include homopolymers of vinylidene fluoride and copolymers containing up to 5% by weight of one or more other monomers copolymerizable therewith, such as "fluorinated monomers."

Endo et al., in U.S. Pat. No. 4,353,960, disclose conjugate fibers containing a core of vinylidene fluoride resin and a sheath of a polyamide resin. The vinylidene fluoride resin may be a homopolymer of a copolymer wherein the comonomer may be, inter alia, hexafluoropropylene. (See col. 3, line 45.)

Mano, in U.S. Pat. No. 4,304,010, discloses a polytetrafluoroethylene tubular prosthesis having a porous elastomer coating. The elastomer coating may be a vinylidene fluoride/hexafluoropropylene copolymer "fluorine rubber." (See col. 3, lines 27-28.)

Endo et al., in U.S. Pat. No. 4,302,556, disclose polyvinylidene fluoride filaments designed particularly for use as fishing lines, wherein the filaments are a mixture of two vinylidene fluoride polymers having different inherent viscosities. The polymers contemplated can be either homopolymers or copolymers. The only copolymer specifically mentioned is a copolymer of vinylidene fluoride and ethylene trifluoride.

DETAILED DESCRIPTION OF THE INVENTION

The vinylidene fluoride copolymers used in the invention are those that contain hexafluoropropylene as a comonomer. The proportions of comonomer have not been found to be narrowly critical. The comonomer is used in an amount sufficient to enhance the compliance and other handleability properties of the surgical filaments made from the copolymer, while still retaining an acceptable level of strength properties. Within these constraints, as a general rule, there will usually be from about 1 weight percent to about 15 weight percent of polymerized comonomer in the copolymer, the remainder being polymerized vinylidene fluoride.

The molecular weight of the copolymer used in the invention will be that ordinarily found in fiber-forming grades. The apparent melt viscosity is usually used to characterize the molecular weight of vinylidene fluoride polymers. It is measured at 200°–230° C. at a shear rate of 100 sec$^{-1}$. Typical values for apparent melt viscosity of fiber-forming grades of the copolymer are within the range of 15,000 to 30,000 poise.

The surgical filaments of the invention are produced from the copolymer by extrusion, drawing, and annealing, in accordance with known techniques. Specific conditions are illustrated in the examples, below. It is within the scope of the invention to employ the copolymer in blends with vinylidene fluoride homopolymer in cases where lower compliance is acceptable. Such blends will usually produce filaments having higher tensile strengths than filaments made from the pure copolymer. The amount of copolymer in the blend will at a minimum be that proportion at which the compliance of the resulting filaments is higher than filaments made from the homopolymer. This improvement in compliance is usually found with as little as 5 weight percent copolymer, based on total weight of the blend.

When the surgical filaments of the invention are intended for use as surgical sutures, they can be attached to a needle, packaged, and sterilized by known procedures, as by ethylene oxide or gamma radiation.

The examples below illustrate the invention.

EXAMPLES 1-7 AND CONTROL EXAMPLE 1

The polymers used in the Examples and Control Example were as follows:

Homopolymer A—A homopolymer of vinylidene fluoride having an apparent melt viscosity at 200° C. and a shear rate of 100 sec$^{-1}$ of about 15,000 poise, and a melting point by ASTM D3418 of 178° C.

Copolymer A—A random copolymer of 90 weight percent vinylidene fluoride and 10 weight percent hexafluoropropylene, having a melting point by ASTM D3418 of 160° C. and an apparent melt viscosity of 22,000 poise at 200° C. and 100 sec$^{-1}$.

Copolymer B—A random copolymer of 95 weight percent vinylidene fluoride and 5 weight percent hexafluoropropylene, having a melting point by ASTM D3418 of 160° C. and an apparent melt viscosity of 22,000 poise at 200° C. and 100 sec$^{-1}$.

Copolymer C—A random copolymer of 87 weight percent vinylidene fluoride and 13 weight percent hexafluoropropylene having a melting point by ASTM D3418 to 136°–143° C. and an apparent melt viscosity of 25,000 poise at 232° C. and 100 sec$^{-1}$.

Filaments were made from the following materials:

COMPOSITION

Control 1: 100% Homopolymer A
Example 1: 90% Homopolymer A + 10% Copolymer A
Example 2: 80% Homopolymer A + 20% Copolymer A
Example 3: 20% Homopolymer A + 80% Copolymer A
Example 4: 10% Homopolymer A + 90% Copolymer A
Example 5: 100% Copolymer A
Example 6: 100% Copolymer B
Example 7: 100% Copolymer C Each composition was extruded on a 1-inch vertical extruder, quenched in water at ambient temperature, drawn in three stages with a heated oven between the third and fourth godets, and wound on spools. The extruded filament was wound on racks, and annealed in an oven with varying amounts of relaxation during the annealing process. Table I, below, outlines the extrusion, drawing, and annealing procedures, and Table II, below, sets forth representative properties of the thus produced filaments.

CONTROL EXAMPLE 2

In an attempt to produce filaments from Homopolymer A which had better compliance, as is illustrated by a decreased Young's modulus, filaments made from Homopolymer A under conditions given in Table I were subjected to varying degrees to relaxation during the annealing step. The annealing conditions and results are displayed in Table III, below. As the data presented in Table III show, the Young's modulus could be reduced by increasing the degree of relaxation; however, there was a concommitant increase in elongation, which is undesirable because the filament then becomes too "stretchy" or elastic. Thus, filaments made from the copolymer of the invention have a better balance of properties, and therefore their utility as a surgical suture or ligature is enhanced.

TABLE I

| | Extrusion | | | | Drawing | |
| --- | --- | --- | --- | --- | --- | --- |
| | Black/Die Temp. (°F.) | Die/Dia./ # Holes (in./—) | Barrel Pump Pr. (psi) | Quench Water Temp. (°F.) | I Godet Speed/Temp. (fpm/°F.) | II Godet Speed/Temp. (fpm/°F.) |
| Control 1 Size 3/0 | 412/413 | 70/1 | 1450/300 | 110 | 40/190 | 194/170 |
| Example 1 Size 2/0 | 383/386 | 30/1 | 1250/1600 | 64 | 22/180 | 130/160 |
| Example 2 Size 4/0 | 431/441 | 30/1 | 1250/2500 | 56 | 40/170 | 252/160 |
| Example 3 Size 2/0 | 411/415 | 30/1 | 1250/1600 | 61 | 16/170 | 76/160 |
| Example 4 Size 2/0 | 406/415 | 30/1 | 1250/1650 | 61 | 16/170 | 76/160 |
| Example 5 Size 2/0 | 377/372 | 30/1 | 1450/1150 | 62 | 17/150 | 80/140 |
| Example 6 Size 2/0 | 423/426 | 30/1 | 1200/2000 | 61 | 11/170 | 52/165 |
| Example 7 Size 2/0 | 488/510 | 30/1 | 1450/1350 | 59 | 6/110 | 42/130 |
| Control 2 Size 5/0 | 421/532 | 30/1 | 1350/600 | 71 | 50/170 | 250/170 |

| | Drawing | | | Annealing | | |
| --- | --- | --- | --- | --- | --- | --- |
| | III Godet Speed/Temp. (fpm/°F.) | Heated Oven (in./°F.) | IV Godet Speed/Temp. (fpm/°F.) | % Relaxation | Anneal. Temp. (°F.) | Time (min.) |
| Control 1 Size 3/0 | 214/280 | 72/280 | 250 | 10 | 290 | 5 |
| Example 1 Size 2/0 | 135/150 | 72/250 | 150/77 | 16 | 285 | 5 |
| Example 2 Size 4/0 | 256/130 | 72/280 | 270/77 | 16 | 285 | 5 |
| Example 3 Size 2/0 | 86/150 | 72/250 | 100/77 | 0 | 125 | 5 |
| Example 4 Size 2/0 | 86/150 | 72/250 | 100/77 | 0 | 125 | 5 |
| Example 5 Size 2/0 | 85/140 | 72/230 | 90/77 | 0 | 125 | 5 |
| Example 6 Size 2/0 | — | 72/240 | 62/77 | 0 | 225 | 5 |
| Example 7 Size 2/0 | 47/77 | 72/240 | 54/77 | NOT ANNEALED | | |
| Control 2 Size 5/0 | 270/150 | 72/290 | 300/77 | SEE TABLE III | | |

TABLE II

| POLYMER SAMPLE | USP SUTURE SIZE | KNOT ST. (psi) | STRAIGHT TENSILE ST. (psi) | BREAK ELONGATION, (%) | YOUNG'S MODULUS (psi) |
| --- | --- | --- | --- | --- | --- |
| Control 1 | 3-0 | 69,000 | 145,000 | 41 | 430,000 |
| Example 1 | 2-0 | 73,000 | 130,000 | 48 | 334,000 |
| Example 2 | 4-0 | 73,000 | 116,000 | 49 | 297,000 |
| Example 3 | 2-0 | 45,000 | 93,000 | 39 | 280,000 |
| Example 4 | 2-0 | 45,000 | 98,000 | 30 | 260,000 |
| Example 5 | 2-0 | 44,000 | 78,000 | 34 | 233,000 |
| Example 6 | 2-0 | 46,000 | 100,000 | 42 | 231,000 |
| Example 7 | 4-0 | 43,000 | 77,000 | 36 | 90,000 |

TABLE III

EFFECT OF RELAXATION ON HOMOPOLYMER PORPERTIES
Control Example 2 - Size 5/0

| % Relaxation | Knot St. (psi) | Tensile St. (psi) | % Elongation | Young's Modulus (psi) |
| --- | --- | --- | --- | --- |
| As extruded | 71,000 | 115,000 | 30 | 390,000 |
| 0 | 64,000 | 147,000 | 30 | 356,000 |
| 16 | 68,000 | 109,000 | 44 | 314,000 |
| 25 | 63,000 | 95,000 | 60 | 249,000 |
| 40 | 57,000 | 79,000 | 81 | 228,000 |

Annealing Temperature = 300° F.
Annealing Time = 5 Minutes

The characteristic properties of the filaments of the invention were determined by conventional test procedures. The tensile properties (i.e., straight and knot tensile strengths, Young's Modulus, and elongation) displayed herein were determined with an INSTRON tensile tester. The settings used to determine the straight tensile, knot tensile, break elongation, and Young's Modulus were the following, unless indicated:

|  | Gauge Length (in) | Chart Speed (in/min) | Crosshead Speed (in/min) |
| --- | --- | --- | --- |
| Straight Tensile | 5 | 10 | 5 |
| Knot Tensile | 5 | 10 | 5 |
| Break Elongation | 5 | 10 | 5 |
| Young's Modulus | 5 | 10 | 5 |

The straight tensile strength is calculated by dividing the force to break by the initial cross-sectional area of the fiber. The elongation to break is read directly from the load-extension curve of the sample.

Young's Modulus is calculated from the slope of the load-extension curve of the sample in the linear elastic region as follows:

$$\text{Young's Modulus} = \frac{\tan\theta \times GL \times CS \times SL}{XH \times XS}$$

$\theta$ is the angle between the slope and the horizontal, XS is the initial cross-sectional area of the fiber, SL is the scale load, XH is the crosshead speed, CS is the chart speed, and GL is the gage length. The SL may be selected to provide a $\theta$ close to 45°.

The knot tensile strength of a fiber is determined in separate experiments. The test article is tied into a surgeon's knot with one turn of the filament around flexible tubing of $\frac{1}{4}$ inch inside diameter and 1/16 inch wall thickness. The surgeon's knot is a square knot in which the free end is first passed twice, instead of once, through the loop, and the ends drawn taut so that a single knot is superimposed upon a compound knot. The first knot is started with the left end over the right end and sufficient tension is exerted to tie the knot securely.

The specimen is placed in the INSTRON tensile tester with the knot approximately midway between the clamps. The knot tensile strength is calculated by dividing the force required to break by the initial cross-sectional area of the fiber.

As a general rule, the surgical filaments of the invention that are made entirely of the copolymer (as opposed to blends with the homopolymer) will exhibit the following properties:
Knot Strength, psi: above 35,000
Straight Tensile Strength, psi: above 50,000
Break Elongation, %: 20-50
Young's Modulus, psi: below 300,000

This is a more desirable combination of properties than that which can be obtained with sutures made from the homopolymer because the tensile properties are more than adequate, the compliance (as indicated by reduced Young's modulus) is much better, and the elongation at break is not so high that the filaments become "stretchy" or elastic. It is probable that the improved balance of properties exhibited by the filaments of the invention derive from a limited disruption in the polymer crystallinity that is caused by the comonomer hexafluoropropylene. This disruption is sufficient to enhance the compliance and handleability of the filaments, but not so great as to cause too much of a reduction in strength properties.

The surgical filaments of the invention can be knitted or woven into surgical protheses such as vascular grafts and meshes. The strength, flexibility, and inertness of the subject filaments considerably enhance the utility of such prostheses.

We claim:

1. A drawn and oriented surgical filament comprising a copolymer of vinylidene fluoride and hexafluoropropylene, wherein said copolymer contains from about 1 to about 15 weight percent polymerized hexafluoropropylene, the remainder being polymerized vinylidene chloride.

2. The surgical filament of claim 1 wherein said filament is made entirely of said copolymer.

3. The surgical filament of claim 1 wherein said filament is made of a blend of said copolymer and vinylidene fluoride homopolymer.

4. The surgical filament of claim 1, 2, or 3 in the form of a sterile suture attached to a needle.

5. The surgical filament of claim 2 having the following properties:
knot strength—above 35,000 psi
straight tensile strength—above 50,000 psi
break elongation—20 to 50%
Young's modulus—below 300,000 psi.

6. The surgical filament of claim 5, wherein said copolymer contains from about 1 to about 15 weight percent polymerized hexafluoropropylene, the remainder being polymerized vinylidene fluoride.

7. The drawn and oriented surgical filament of claim 5, wherein the copolymer consists essentially of a random copolymer of about 10 weight percent polymerized hexafluoropropylene and about 90 weight percent polymerized vinylidene fluoride.

8. The drawn and oriented surgical filament of claim 5, wherein the copolymer consists essentially of a random copolymer of about 5 weight percent polymerized hexafluoropropylene and about 95 weight percent polymerized vinylidene fluoride.

9. The drawn and oriented surgical filament of claim 5, wherein the copolymer consists essentially of a random copolymer of about 13 weight percent polymerized hexafluoropropylene and about 87 weight percent polymerized vinylidene fluoride.

* * * * *